United States Patent
Farber et al.

(10) Patent No.: US 6,200,816 B1
(45) Date of Patent: Mar. 13, 2001

(54) METHOD FOR MEASURING PARTICULATE AND GASEOUS METALS IN A FLUID STREAM, DEVICE FOR MEASURING PARTICULATE AND GASEOUS METALS IN A FLUID STREAM

(75) Inventors: Paul S. Farber, Willowbrook; Hann-Shen Huang, Westmont, both of IL (US)

(73) Assignee: The United States of America as represented by the Department of Energy, Washington, DC (US)

( * ) Notice: Subject to any disclaimer, the term of this patent is extended or adjusted under 35 U.S.C. 154(b) by 0 days.

(21) Appl. No.: 09/176,255

(22) Filed: Oct. 21, 1998

(51) Int. Cl.[7] .................................................. G01N 33/20

(52) U.S. Cl. .......................... 436/73; 422/88; 422/62; 436/25; 436/26; 436/81; 436/83; 436/177; 436/178; 436/182

(58) Field of Search ................................. 436/25, 26, 44, 436/73, 81, 83, 177–178, 182; 422/69, 88, 62

(56) References Cited

U.S. PATENT DOCUMENTS

| | | | |
|---|---|---|---|
| 3,061,723 | * 10/1962 | Kapff | 436/44 |
| 3,098,719 | * 7/1963 | Skeggs | 436/44 |
| 3,940,614 | * 2/1976 | Rhodes et al. | 250/273 |
| 4,056,969 | * 11/1977 | Barringer | 73/28 |
| 4,568,520 | * 2/1986 | Ackermann et al. | 436/44 X |
| 4,742,009 | * 5/1988 | Beverly et al. | 436/44 X |
| 5,637,506 | * 6/1997 | Goken et al. | 436/73 X |

OTHER PUBLICATIONS

W. Dannecker et al. Staub—Reinhalt. Luft 1983, 43, 253–258, Jun. 1983.*
K. E. Lorber Waste Manage. Res. 1986, 4, 3–13, Jan. 1986.*
K. Yasuda et al. Taiki Osen Gakkaishi 1986, 21, 191–196, Mar. 1986.*
W. J. Smith et al. Am. Ind. Hyg. Assoc. J. 1986, 47, 779–784, Dec. 1986.*
J. A. Cooper Fuel Process. Technol. 1994, 39, 251–258.*
M. B> Bernick et al. J. Hazard. Mater. 1995, 43,91–99.*
E. M. Prestbo et al. Water, Air, Soil Pollut. 1995, 80, 145–158.*
B. S. Turk et al. High Temp. Gas Clean., 3rd, E. Schmidt ed., Institut fuer Mechanische Verfahrenstchnik und Mechanik der Unviversitaet Karlsruhe: Karlsruhe, Germany, 1996, pp. 302–315.*
O. Haupt et al. X–Ray Spectrom. 1997, 26, 79–84, Feb. 1997.*
G. M. Thomson et al. Am. Ind. Hyg. Assoc. J. 1997, 58, 98–104, Feb. 1997.*

* cited by examiner

*Primary Examiner*—Arlen Soderquist
(74) *Attorney, Agent, or Firm*—Mark F. LaMarre; Mark P. Dvorscak; Paul A. Gottlieb

(57) ABSTRACT

A method for analyzing metal in a fluid is provided comprising maintaining a first portion of a continuous filter media substrate at a temperature coinciding with the phase in which the metal is to be analyzed; contacting the fluid to a first portion of said substrate to retain the metal on the first portion of said substrate; preventing further contact of the fluid to the first portion of substrate; and contacting the fluid to a second portion of said substrate to retain metal on the second portion of the said substrate while simultaneously analyzing the first portion for metal. Also provided is a device for the simultaneous monitoring and analysis of metal in a fluid comprising a continuous filter media substrate; means for maintaining a first portion of said filter media substrate at a temperature coinciding with the phase in which the metal is to be analyzed; a means for contacting the fluid to the first portion of said substrate; a means for preventing further contact of the fluid to the first portion of substrate; a means for contacting the fluid to a second portion of said substrate to retain metal on the second portion of the said substrate; and means for analyzing the first portion for metal.

14 Claims, 2 Drawing Sheets

METHOD FOR MEASURING PARTICULATE AND GASEOUS METALS IN A FLUID STREAM, DEVICE FOR MEASURING PARTICULATE AND GASEOUS METALS IN A FLUID STREAM

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to a method and device for measuring metals in a fluid stream, and more specifically, this invention relates to a method and device for simultaneously measuring metals in a gas stream while also providing archival samples.

2. Background of the Invention

The problems associated with the presence of metal particulates in air due to combustion and other activities continue to increase. As a result, the U.S. Environmental Protection Agency requires analysis of a number of metals in gas streams from combustors, incinerators, and other such entities.

Also, many industrial processes depend on the analysis of process streams before and/or after certain operations.

Present sampling techniques include manual stack sampling, which involves wet chemical analysis and the concomitant long delay in getting the results. Furthermore, such analysis usually results in destruction of the sample so that sample archiving is not possible. Nondestructive analysis is sometimes valuable in instances where confirmation of test results is desired long after initial sampling and reporting is made.

Generally, particulates in gas streams are analyzed by diverting a known portion of the stream to pass through a filter media onto which the particulate sample is collected. The sample is then moved to a means for analyzing the sample. Usually, the collection process needs to be halted so as to facilitate removal of the filter media.

Typically, gaseous metals entrained in the stream are collected by passing a known portion of the stream into some means for collecting such samples, such as a cold condenser or a liquid impinger where the metal sample condenses out or precipitates out. The metal sample must then be collected from the condenser or recovered from the liquid before an analysis of the sample can be made.

Devices exist for detecting the presence of certain analytes in a sample. For example, U.S. Pat. No. 5,541,057 to Bogart et al., utilizes an optically active surface to facilitate assays of biological analytes. U.S. Pat. No. 5,460,973 utilizes a combination of distillation and head space analysis to measure volatile impurities.

Other devices exist for collecting metals in the atmosphere. One such device, U.S. Pat. No. 3,940,614 to Rhodes, utilizes a high volume air sampler combined with noble-metal-coated fibrous packing. The device facilitates the collection of mercury vapor. However, no provision is made for particulate collection or analysis.

A need exists in the art for an inexpensive method and device to simultaneously measure particulate and vapor phases of metals contained in a fluid. The method and device should be adaptable to on-line operations and to installation on mobile units. The method and device should also provide for archive sampling.

SUMMARY OF THE INVENTION

It is an object of the invention to provide a method and a device for the measurement of the solid-phase and vapor-phase metals that overcomes many of the disadvantages of the prior art.

Another object of the present invention is to provide a method and device to simultaneously measure metal particulates and metal vapor in a flue stream. A feature of the invention is the use of a continuous sampling media. An advantage of the invention is the facilitation of near real-time sampling of the metal content in the flue stream.

Yet another object of the present invention is to provide an economical method and device for analyzing metals in a gas stream. A feature of the invention is contacting the gas stream with a continuous surface comprising an adsorbent and subsequently analyzing the surface with a standard x-ray fluorescence analyzer. Another feature of the invention is that the surface can be temperature adjusted to capture and remove volatile matter such as lower boiling point chemicals and metals. An advantage of the invention is the use of standard materials and methods to provide a rapid analysis of metal content in the gas stream.

Still, another object of the present invention is to provide a method and device for capturing and retaining target matter for analysis. A feature of the invention is utilizing a plurality of adsorbents to capture the matter. An advantage of the invention is the capture and retention of different types of matter for instant analysis or archival purposes.

Briefly, the invention provides for a method for analyzing metal in a fluid comprising supplying a continuous filter media substrate; maintaining a first portion of said filter media substrate at a temperature coinciding with the phase in which the metal is to be analyzed; contacting the fluid to the first portion of said substrate to retain the metal on the first portion of said substrate; preventing further contact of the fluid to the first portion of said substrate; and contacting the fluid to a second portion of said substrate to retain metal on the second portion of the said substrate while simultaneously analyzing the first portion for metal, whereby the second portion of said substrate is integral to the first portion of said substrate.

The invention also provides for a device for analyzing metal in a fluid comprising a continuous filter media substrate; means for maintaining a first portion of said filter media substrate at a temperature coinciding with the phase in which the metal is to be analyzed; a means for contacting the fluid to the first portion of said substrate; a means for preventing further contact of the fluid to the first portion of said substrate; a means for contacting the fluid to a second portion of said substrate to retain metal on the second portion of the said substrate; and means for analyzing the first portion for metal, whereby the second portion of said substrate is integral to the first portion of said substrate.

These and other features and advantages of the invention will be apparent from the detailed description of the invention and from the claims.

BRIEF DESCRIPTION OF THE DRAWING

The invention together with the above and other objects and advantages will be best understood from the following detailed description of the preferred embodiment of the invention shown in the accompanying drawing, wherein.

DETAILED DESCRIPTION OF THE INVENTION

Generally, the invention provides for near real time, on-line monitoring of metal emissions and chemical emissions and for archiving of the sample results. The invented method is applicable for both environmental remediation efforts and for determining process losses. For example, many jurisdictions around the world are considering requiring the continuous monitoring of metals and volatile compounds in flue gas streams. Furthermore, these jurisdictions require confirmation of sample findings, which the instant invention's archiving capabilities allow.

Specifically, a method and device are provided for analyzing metals and their concentration in a fluid stream. Analysis of other types of matter, such as volatile materials, is also provided.

More specifically, the method and device could be used to monitor effluent from a number of entities, including, but not limited to furnaces, incinerators, smelters, iron and steel plants, lime and cement kilns, battery plants and semiconductor plants. An exemplary application of the invention is the analysis of fly-ash from coal combustion.

Figure 1:
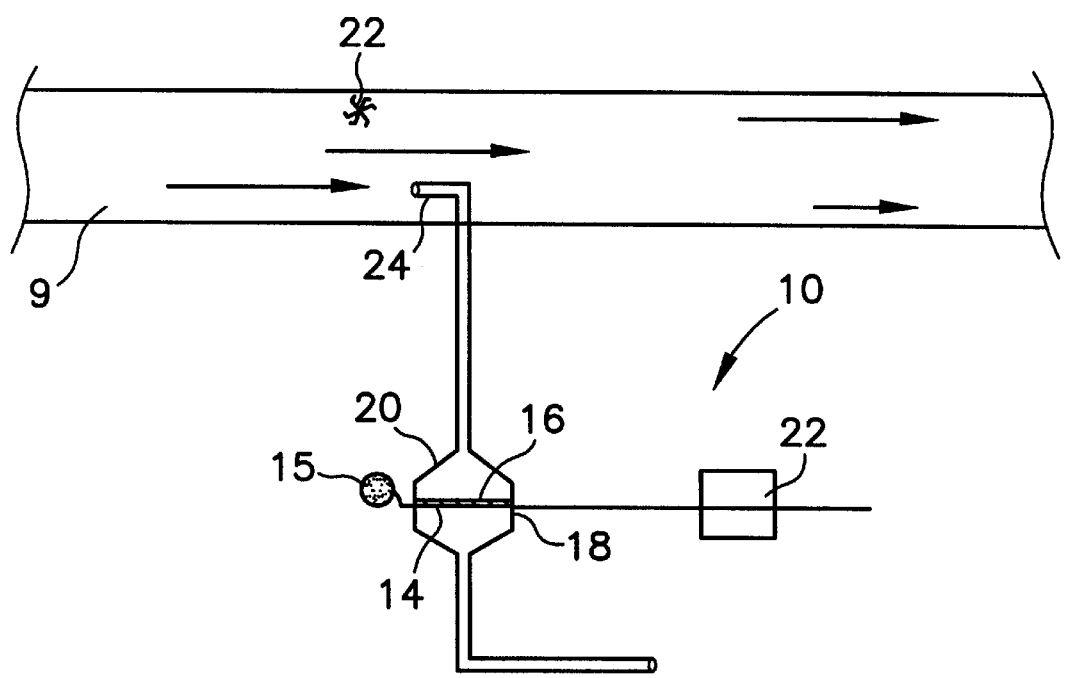
FIG. 1 is a schematic depiction of an apparatus for analyzing metal particulate and vapor, in accordance with features of the present invention.

A schematic depiction of the invention is shown in FIG. 1 as numeral 10. Generally, a known portion of a gas stream 9 is diverted, preferably under isokinetic conditions, to a device containing a movable filter configuration. Normally, the gas stream is kept at a temperature sufficient to minimize the possibility of metal vapors condensing out prior to treatment by the sample conditioning and measurement system.

A filter media 14 is used to collect particulate. The filter media 14 is arranged in a continual feed arrangement such as a feeder roll 15. An exit point 18 of the filter media 14 from a filter housing 20 is situated so as to facilitate immediate analysis of the material captured by the now-exposed filter media. This arrangement allows for the exposed filter media to be constantly or periodically moved to another portion of the sample conditioning and measurement device where concentrations are then determined. This feature contributes to the real-time advantage of the invented device. This feature also allows for the filter media to constantly be replaced with unexposed filter media without interruption in sample taking.

Exemplary means for analyzing the filter media include, but are not limited to x-ray fluorescence, emission spectroscopy, absorption spectroscopy, inductively coupled plasma spectroscopy, x-ray absorption fine structure spectroscopy (XAFS), and combinations thereof.

Optionally, and during contact with the flue gas, the filter media 14 is maintained at higher or lower temperatures relative to the in-flowing gas stream so as to allow collection of lower-boiling point materials as a solid, or higher boiling point materials as a vapor, respectively, depending on the needs of the specific application.

Figure 2:
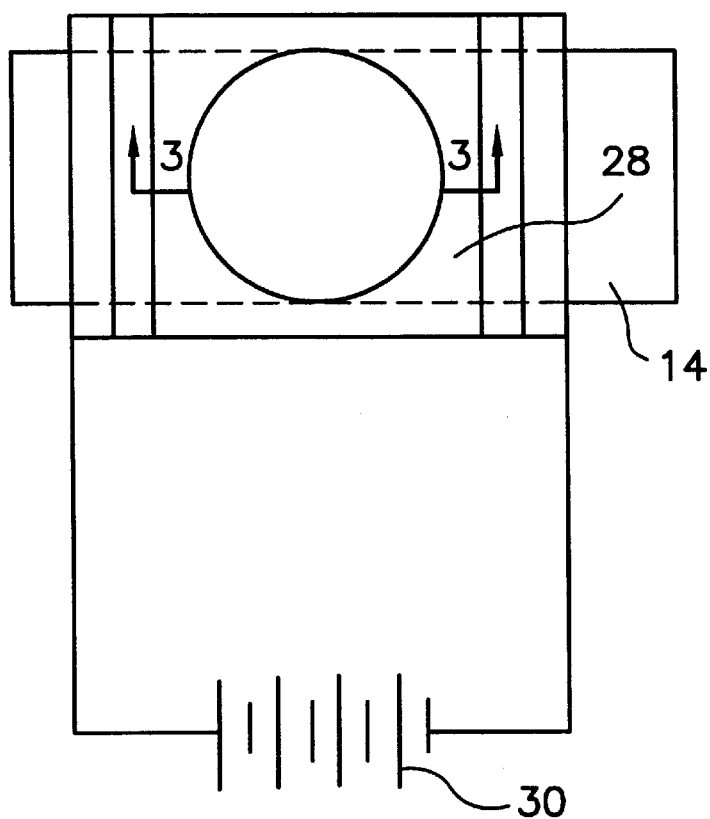
FIG. 2 is a plan view of an exemplary thermoelectric cooling plate, in accordance with features of the present invention.
Figure 3:
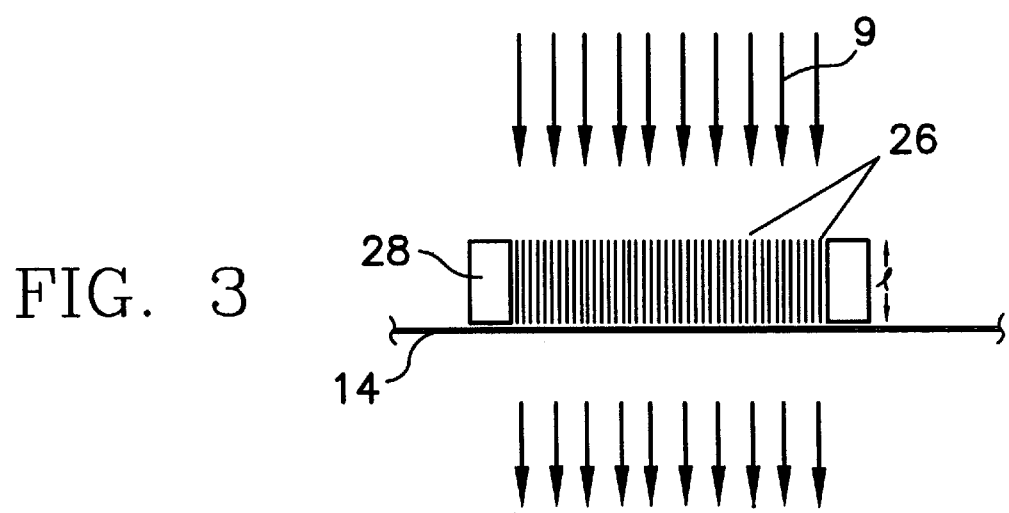
FIG. 3 is a view of FIG. 2 taken along line 3—3.

A myriad of means are utilized to maintain the temperature at a desired temperature. For example, a porous thermoelectric device 16 can be placed in contact with the filter media 14, either on the filter media's upstream side or downstream side so as to cause entrained gaseous metals to condense out on the filter media simultaneously with the collection of the particulate sample. One such thermoelectric device is depicted in FIGS. 2 and 3. As shown therein, the thermoelectric cooler contains a plurality of gas flow passages 26 defining a temperature transfer means 28. The temperature transfer means 28 is utilized to either lower or raise the temperature of the filter media 14 in communication with the temperature transfer means 28. The thermoelectric device is energized via standard electric current, 30 and either in DC or AC mode.

The diameter of the flow passages, as well as the length of the passages 26 are sufficient to effect the desired phase change of certain target materials in the impinging gas stream 9. As such, the diameters and lengths of the flow passages will vary depending on the temperature of the incoming stream 9 and the target materials the phases of which are to be manipulated to facilitate material capture.

Instead of effecting the temperature of the filter media via a porous thermoelectric device or some other conductive means, the filter media itself can be directly cooled (or warmed) prior to being placed in the path of the fluid stream, for example by refrigerating (or heating) the filter media roll 15 prior to its use.

Yet another alternative to modifying the temperature of the filter media is to utilize a means for cooling the filter holder 20 to the desired temperature.

Combining the above-described system with a gas flow measuring device could result in a real-time on-line system for comparing gas flow rates with metal concentrations or other types of emissions. Generally, a myriad of gas-flow rates can be accommodated with the invented system and device, with a minimum flow rate of 0.1 liter per minute (L/min).

Preferably the temperature of the filter media should be maintained above zero degrees centigrade, with specific filter media temperatures varying, depending on the phase in which the "captured" materials are to be isolated from the feed stream. For example, if mercury vapor is present in the feed stream 9, then filter media should be cooled down to below the boiling point of mercury (approximately 357° C.) prior to exposure to the filter.

The invented system is superior to prior art systems in that the collection process does not have to be halted to facilitate collection of the filter media. Also, no condensors or other expensive devices are needed to facilitate removal of gaseous components.

Adsorbent Detail

Generally, percolation filtration is utilized in the instant method and device.

As such, a myriad of adsorbing solids or "solid foams" can be utilized. Substances having surface areas of between 50 square meters per gram and 250 square meters per gram are suitable.

Depending on the source of the effluent, the adsorbed metals or other materials derived from the fluid stream are bound to the adsorbent in different ways: Merely physical or van der Waals forces are the agents of interaction. Often, active adsorption, also termed "chemisorption" occurs wherein adsorption depends at least partially on activation energies of the interactions between the adsorbing solid and the material to be derived from the fluid stream.

Most commercial adsorbents are suitable for use in the instant method and device, including, but not limited to Fuller's earth, Bauxite, Acid-treated clays, Bone char (bone black), activated carbon, Alumina, Silica gel, Base-exchange silicates, Magnesia, medicinal carbons, metal-adsorbent chars.

In instances where metals and volatiles are entrained in the same feed stream to be analyzed, and it is desirous for archival sampling to occur, adsorbents specific for various target chemicals can be combined and deposited on filter media. For example, adsorbent resins such as sulfonated divinylbezenes/styrene copolymer or generalized cationic/anionic exchange resins specific for volatile compounds can be combined with other adsorbents (such as activated carbon) to provide a means for collecting a myriad of substances which differ in both phase and chemistry in a particular collection scenario. One suitable cation exchange resin is Amberlite® available from Mallinckrodt Baker, Inc, Phillipsburg, N.J. These adsorbent resins are applied in a myriad of ways, including powder-coating, or spray-deposited directly onto the filter substrate.

In such multi-target sampling scenarios, the filter substrate, elaborated on below, would capture metal particles, while the adsorbent resins, discussed supra, would capture the gaseous phases of the metals and other, volatile chemicals.

The resulting post-exposed sampling substrate (consisting of the filter material and the adsorbent combination) could then be analyzed immediately for the presence of metals and volatiles. Alternatively, portions of the post-exposed sampling substrate could be analyzed in near real-time while archiving the remaining portion for confirmation at an indefinite time. Archiving via refrigeration under dry conditions provides suitable results.

Filter Substrate Detail

Generally, the adsorbent material is deposited on a continuous, porous flexible substrate, so as not to compromise the porosity of the substrate. Otherwise, flow-through of the subject fluid through the filter media would be inhibited. Exemplary, flexible foundation substrates include, but are not limited to paper, glass fiber filter tape, screen or some grid configuration coated with material which is inert to the adsorbent material and constituents of the feed stream. Glass fiber filters of the type specified in the U.S. EPA Method 5 protocol, (40 C.F.R. Part 60, Appendix A) and incorporated herein by reference, are suitable foundation substrates.

The adsorbent can be powder-coated or spray-coated to the substrate during the later's manufacture.

The amount of the adsorbing material deposited on the filter substrate will depend on the surface area of the adsorbing material. As such, thickness of the deposited, adsorbent material will vary, but generally, thicknesses of from 10 microns ($\mu$m) to 100 $\mu$m will suffice. This will allow for the capture of metal particles having a diameters as small as 0.05 $\mu$m.

Feed Stream
Probe Detail

As discussed supra, the invention provides for a means to extract a representative sample from a feed stream for analysis. Sampling under isokinetic conditions may be preferable. Such isokinetic sampling provides for the extraction of a sample at the same speed maintained by the feed stream; with resulting in representative sampling.

For an even more representative analysis, and particularly for monitoring process applications, a means for measuring stream flow 22 is provided. This provision allows for the determination of not only target matter concentration data, but also mass data of the target matter.

A myriad of means for extracting 24 the sample from the feed stream are commercially available. For example, type S Pitot tubes, similar to impact tubes, are suitable, and available through Graseby Anderson, Smyrna, Ga. Generally, a suitable probe is one which can be utilized as part of an apparatus for testing emissions from stationary sources, as defined by the Method Five protocol of the U.S. Environmental Protection Agency, noted supra.

While the invention has been described with reference to details of the illustrated embodiment, these details are not intended to limit the scope of the invention as defined in the appended claims. For example, the invention can be utilized to capture or analyze fluid streams for the types and amounts of inorganic and/or organic compounds contained therein. The isolation of such compounds as radioactive material, dioxins, lead, and heavy metals may be particularly facilitated with the application of the invented method and device. The measurement of the radioactive material can be made downstream of measurements made on captured metals, and such radioactivity may be measured using a standard scintillation device or other radioactivity measuring means. Sensitivity of the invented method and device depends on the state of the art sampling equipment utilized and also the amount of time the invented method and/or device are utilized to obtain a sample.

The embodiment of the invention in which an exclusive property or privilege is claimed is defined as follows:

1. A method for analyzing metal in a fluid comprising:
    a) providing a fluid comprising solid metal particulates and gaseous metal;
    b) supplying a continuous filter media substrate;
    c) maintaining a first portion of said filter media substrate at a temperature coinciding with the phase in which the metal is to be analyzed in order to condense the gaseous metal to be analyzed and thereby simultaneously collecting solid metal particles and gaseous metal;
    d) contacting the fluid to the first portion of said substrate to retain the metal in the form of solid metal particles and condensed gaseous metal on the first portion of said substrate;
    e) preventing further contact of the fluid to the first portion of substrate; and
    f) contacting the fluid to a second portion of said substrate to retain metal on the second portion of the said substrate while simultaneously analyzing the first portion for metal, whereby the second portion of said substrate is integral to the first portion of said substrate.

2. The method as recited in claim 1, wherein the substrate has a surface area of between approximately 50 square meters per gram to 250 square meters per gram.

3. The method as recited in claim 1 wherein the substrate is an adsorbent deposited on a continuous roll of support material.

4. The method as recited in claim 1 wherein the substrate is an adsorbent selected from the group consisting of Fuller's earth, charcoal, Alumina, Bauxite, acid-treated clays, bone char, Silica gel, base-exchange silicates, Magnesia, metal adsorbent chars, or combinations thereof.

5. The method as recited in claim 1 wherein the metal is selected from the group consisting of mercury, cadmium, lead, nickel, chromium, and combinations thereof.

6. The method as recited in claim 1, wherein the fluid is a flue stream.

7. The method as recited in claim 6 wherein the flue stream originates from operations dealing with furnaces, incinerators, smelters, iron and steel plants, lime and cement kilns, battery plants or semi-conductor plants.

8. The method as recited in claim 1, wherein the fluid is a gas selected from the group consisting of air, noble gases, flue gas, combustion exhaust gases, nitrogen, oxygen, hydrogen, and combinations thereof.

9. The method as recited in claim 1 wherein the filter media is constantly being replaced.

10. A device for analyzing metal in a fluid comprising:
   a) a continuous filter media substrate;
   b) a means for maintaining a first portion of said filter media substrate at a temperature coinciding with the phase in which the metal is to be analyzed;
   c) a means for contacting the fluid to the first portion of said substrate;
   d) a means for preventing further contact of the fluid to the first portion of substrate; and
   e) a means for contacting the fluid to a second portion of said substrate to retain metal on the second portion of the said substrate; and
   f) a means for analyzing the first portion for metal, whereby the second portion of said substrate is integral to the first portion of said substrate.

11. The device as recited in claim 10, wherein the substrate has a surface area of between approximately 50 square meters per gram to 250 square meters per gram.

12. The device as recited in claim 10 wherein the substrate is an adsorbent deposited on a continuous roll of support material.

13. The device as recited in claim 12 wherein the adsorbent is Fuller's earth, charcoal, Alumina, Bauxite, acid-treated clays, bone char, Silica gel, base-exchange silicates, Magnesia, metal adsorbent chars, or combinations thereof.

14. The device as recited in claim 10 wherein the filter media is constantly moving.

* * * * *